US012680120B2

(12) United States Patent
Ryu et al.

(10) Patent No.: US 12,680,120 B2
(45) Date of Patent: Jul. 14, 2026

(54) *CORYNEBACTERIUM GLUTAMICUM* MUTANT STRAIN HAVING ENHANCED L-LYSINE PRODUCTIVITY AND METHOD OF PRODUCING L-LYSINE USING THE SAME

(71) Applicant: DAESANG CORPORATION, Seoul (KR)

(72) Inventors: Mi Ryu, Daejeon (KR); In Pyo Hong, Gyeonggi-do (KR); Min Jin Choi, Gyeonggi-do (KR); Seok Hyun Park, Gyeonggi-do (KR); Jae Chun Han, Seoul (KR)

(73) Assignee: DAESANG CORPORATION, Seoul (KR)

( * ) Notice: Subject to any disclaimer, the term of this patent is extended or adjusted under 35 U.S.C. 154(b) by 532 days.

(21) Appl. No.: 18/024,400

(22) PCT Filed: Apr. 20, 2021

(86) PCT No.: PCT/KR2021/004965
§ 371 (c)(1),
(2) Date: Mar. 2, 2023

(87) PCT Pub. No.: WO2022/050527
PCT Pub. Date: Mar. 10, 2022

(65) Prior Publication Data
US 2023/0313244 A1      Oct. 5, 2023

(30) Foreign Application Priority Data

Sep. 3, 2020   (KR) ........................ 10-2020-0112339
Apr. 19, 2021   (KR) ........................ 10-2021-0050318

(51) Int. Cl.
*C12P 13/08*       (2006.01)
*C12N 9/10*       (2006.01)
*C12N 15/77*       (2006.01)

(52) U.S. Cl.
CPC ............ *C12P 13/08* (2013.01); *C12N 9/1025* (2013.01); *C12N 15/77* (2013.01); *C12Y 203/03001* (2013.01); *C12N 2800/101* (2013.01)

(58) Field of Classification Search
None
See application file for complete search history.

(56) References Cited

U.S. PATENT DOCUMENTS 7,566,557 B2 *   7/2009   Klopprogge ........... C07K 14/34
                                                            435/320.1
9,169,502 B2 *   10/2015   Wittmann ............... C12P 13/08
2008/0014618 A1   1/2008   Bathe et al.

2009/0215133 A1   8/2009   Bathe et al.
2009/0280542 A1   11/2009   Bathe et al.
2012/0214211 A1   8/2012   Bathe et al.

FOREIGN PATENT DOCUMENTS

| CN | 110546254 | 12/2019 | |
| EP | 3 561 055 | 10/2019 | |
| JP | 6-197779 | 7/1994 | |
| JP | 2011-518571 | 6/2011 | |
| JP | 2013-524781 | 6/2013 | |
| KR | 10-1993-0016536 | 8/1993 | |
| KR | 10-0838038 | 6/2008 | |
| KR | 10-1915433 | 11/2018 | |
| KR | 10-2139806 | 7/2020 | |
| WO | WO-2008006680 A2 * | 1/2008 | ........... C12N 9/1217 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Becker et al. Eng. Life Sci. 2010, 70, No. 5, 430-438, abstract (Year: 2010).*
International Search Report issued Aug. 11, 2021 in International (PCT) Application No. PCT/KR2021/004965.
Van Ooyen, Jan et al., "Improved L-Lysine production with *Corynebacterium glutamicum* and systemic insight into citrate synthase flux and activity", Biotechnology and Bioengineering, Aug. 2012, vol. 109, No. 8, pp. 2070-2081.
Chinese Office Action issued Mar. 15, 2023 in corresponding Chinese Patent Application No. 202110489001.7, with English translation.

(Continued)

*Primary Examiner* — Christian L Fronda
(74) *Attorney, Agent, or Firm* — Wenderoth, Lind & Ponack, L.L.P.

(57)      ABSTRACT

The present disclosure relates to a *Corynebacterium glutamicum* mutant strain having enhanced L-lysine productivity and a method of producing L-lysine using the same. The *Corynebacterium glutamicum* mutant strain may produce L-lysine in an improved yield by inhibiting the conversion of oxaloacetate to citrate due to decreased or inhibited expression of the gene encoding the citrate synthase.

1 Claim, 2 Drawing Sheets
Specification includes a Sequence Listing.

(56)     References Cited

OTHER PUBLICATIONS

Office Action issued Mar. 4, 2024 in corresponding Japanese Patent Application No. 2023-514804, with English translation.

Judith Becker et al., "From zero to hero-Design-based systems metabolic engineering of Corynebacterium glutamicum for L-lysine production", Metabolic Engineering, 2011, vol. 13, pp. 159-168.

Office Action issued Mar. 6, 2023 in Korean Patent Application No. 10-2021-0050318, with English translation.

Horswill, A.R et al., "Studies of Propionate Toxicity in *Salmonella enterica* Identify 2-Methylcitrate as a Potent Inhibitor of Cell Growth", J. Biol. Chem. 2001, vol. 276, No. 22, pp. 19094-19101.

Decision of Refusal issued Sep. 17, 2024 in Japanese Application No. 2023-514804 (with English translation).

\* cited by examiner

CORYNEBACTERIUM GLUTAMICUM MUTANT STRAIN HAVING ENHANCED L-LYSINE PRODUCTIVITY AND METHOD OF PRODUCING L-LYSINE USING THE SAME

BACKGROUND

1. Technical Field

The present disclosure relates to a *Corynebacterium glutamicum* mutant strain having enhanced L-lysine productivity and a method of producing L-lysine using the same.

2. Related Art

L-lysine is an essential amino acid that is not synthesized in the human or animal body. L-lysine needs to be supplied externally and is generally produced by fermentation using microorganisms such as bacteria or yeast. L-lysine production may be performed using naturally occurring wild-type strains or mutant strains obtained by modifying the wild-type strains to have enhanced L-lysine productivity. In recent years, in order to improve the production efficiency of L-lysine, various recombinant strains or mutant strains having excellent L-lysine productivity and methods of producing L-lysine using the same have been developed by applying gene recombination technology to microorganisms such as *Escherichia coli* and *Corynebacterium*, which are widely used for the production of L-amino acids and other useful substances. According to Korean Patent Nos. 10-0838038 and 10-2139806, L-lysine productivity may be enhanced by increasing the expression of genes of L-lysine production-related enzymes or removing L-lysine production-unnecessary genes.

L-lysine is an aspartate-derived amino acid, and the level of synthesis of oxaloacetate, a precursor of aspartate, also affects the production of L-lysine. Oxaloacetate is produced in a microbial glycolytic pathway and is condensed with acetyl-CoA by citrate synthase to produce citrate. Therefore, it is expected that the amount of L-lysine produced may also be controlled by controlling the expression level of the citrate synthase that converts oxaloacetate to citrate.

PRIOR ART DOCUMENTS

Patent Documents

Korean Patent No. 10-0838038
Korean Patent No. 10-2139806

SUMMARY

An object of the present disclosure is to provide a *Corynebacterium glutamicum* mutant strain having enhanced L-lysine productivity.

Another object of the present disclosure is to provide a method of producing L-lysine using the mutant strain.

The present inventors have conducted studies to develop a novel mutant strain having enhanced L-lysine productivity using a *Corynebacterium glutamicum* strain, and as a result, have found that, when the sequence of a gene encoding citrate synthase, particularly the start codon ATG, is replaced with GTG or TTG in order to weaken the activity of the citrate synthase, the amount of L-lysine produced increases, thereby completing the present disclosure.

One aspect of the present disclosure provides a *Corynebacterium glutamicum* mutant strain having enhanced L-lysine productivity due to weakened activity of citrate synthase.

As used herein, the term "citrate synthase" refers to an enzyme that acts in the TCA cycle and catalyzes a reaction that synthesizes citrate by condensing oxaloacetate with acetyl-CoA produced in the glycolytic pathway.

According to one embodiment of the present disclosure, the citrate synthase may be derived from a strain of the genus *Corynebacterium*. Specifically, the strain of the genus *Corynebacterium* may be, but is not limited to, *Corynebacterium glutamicum*, *Corynebacterium crudilactis*, *Corynebacterium deserti*, *Corynebacterium callunae*, *Corynebacterium suranareeae*, *Corynebacterium lubricantis*, *Corynebacterium doosanense*, *Corynebacterium efficiens*, *Corynebacterium uterequi*, *Corynebacterium stationis*, *Corynebacterium pacaense*, *Corynebacterium singulare*, *Corynebacterium humireducens*, *Corynebacterium marinum*, *Corynebacterium halotolerans*, *Corynebacterium spheniscorum*, *Corynebacterium freiburgense*, *Corynebacterium striatum*, *Corynebacterium canis*, *Corynebacterium ammoniagenes*, *Corynebacterium renale*, *Corynebacterium pollutisoli*, *Corynebacterium imitans*, *Corynebacterium caspium*, *Corynebacterium testudinoris*, *Corynebacterium pseudopelargi*, or *Corynebacterium flavescens*.

As used herein, the term "weakened activity" means the expression level of a gene of interest is decreased compared to the original expression level of the gene. The term "weakened activity" also includes: a case in which the activity of a protein itself is decreased compared to the activity of the protein in the parent microorganism by substitution, insertion, deletion, or a combination thereof of one or more of the nucleotides encoding the gene; a case in which the overall enzyme activity in the cell is lower than that in the wild-type strain or the strain before modification due to decreased expression or translation of the gene encoding the protein; and a combination thereof.

According to one embodiment of the present disclosure, the weakened activity of the citrate synthase may be achieved by replacement of the start codon of a gene encoding the citrate synthase with GTG.

According to one embodiment of the present disclosure, the weakened activity of the citrate synthase may be achieved by replacement of the start codon of a gene encoding the citrate synthase with TTG.

According to one embodiment of the present disclosure, the gene encoding the citrate synthase may be represented by the nucleotide sequence of SEQ ID NO: 1.

According to one embodiment of the present disclosure, the gene encoding the citrate synthase may be represented by the amino acid sequence of SEQ ID NO: 2.

In one example of the present disclosure, a *Corynebacterium glutamicum* mutant strain having a new start codon of the citrate synthase (gltA) gene was obtained by ATG-to-GTG replacement in the start codon in the nucleotide sequence of SEQ ID NO: 1 encoding the the citrate synthase (gltA) gene of a *Corynebacterium glutamicum* strain. This *Corynebacterium glutamicum* mutant strain may contain a citrate synthase gene having the nucleotide sequence of SEQ ID NO: 3 or encoding the amino acid sequence of SEQ ID NO: 4.

In one example of the present disclosure, a *Corynebacterium glutamicum* mutant strain having a new start codon of the citrate synthase (gltA) gene was obtained by ATG-to-TTG replacement in the start codon in the nucleotide sequence of SEQ ID NO: 1 encoding the citrate synthase (gltA) gene of a *Corynebacterium glutamicum* strain. It was confirmed that this *Corynebacterium glutamicum* mutant strain contains a citrate synthase gene having the nucleotide sequence of SEQ ID NO: 5 or encoding the amino acid sequence of SEQ ID NO: 6.

As used herein, the term "enhanced productivity" means that L-lysine productivity of the mutant strain is higher than that of the parent strain. The parent strain refers to a wild-type strain to be mutated or a mutant strain, and includes a strain that is to be mutated directly or to be transformed with a recombinant vector or the like. In the present disclosure, the parent strain may be a wild-type *Corynebacterium glutamicum* strain or a strain mutated from the wild-type strain. For example, the parent strain may be a mutant strain having mutations in the sequences of genes (e.g., lysC, zwf and hom genes) that are involved in lysine production. Specifically, the parent strain may be a *Corynebacterium glutamicum* strain (hereinafter referred to as '*Corynebacterium glutamicum* DS1 strain') deposited with the Korean Culture Center of Microorganisms on Apr. 2, 2021 under accession number KCCM12969P.

In one example of the present disclosure, the *Corynebacterium glutamicum* mutant strain having enhanced L-lysine productivity may exhibit increased L-lysine productivity compared to the parent strain. In particular, the *Corynebacterium glutamicum* mutant strain may show an increase in L-lysine production of 5% or more, specifically 5 to 20%, compared to the parent strain, and thus produce 66 to 80 g, preferably 68 to 78 g of L-lysine, per liter of the strain culture medium.

The *Corynebacterium glutamicum* mutant strain according to one embodiment of the present disclosure may be obtained through a recombinant vector comprising a variant resulting from replacement of the start codon of the citrate synthase gene in the parent strain with GTG or TTG.

As used herein, the term "variant" refers to a genetic variant resulting from replacement of the start codon ATG of the citrate synthase gene, which is involved in L-lysine biosynthesis, with GTG or TTG.

According to an embodiment of the present disclosure, the variant resulting from replacement of the start codon of the citrate synthase gene with GTG may have the nucleotide sequence of SEQ ID NO: 3 or the amino acid sequence of SEQ ID NO: 4.

According to one embodiment of the present disclosure, the variant resulting from replacement of the start codon of the citrate synthase gene with TTG may have the nucleotide sequence of SEQ ID NO: 5 or the amino acid sequence of SEQ ID NO: 6.

As used herein, the term "vector" refers to an expression vector capable of expressing a protein of interest in a suitable host cell, and means a gene construct that contains essential control elements operably linked so that an inserted gene is expressed. As used herein, the term "operably linked" means that a gene to be expressed and the regulatory sequence thereof are functionally linked to each other in a manner enabling gene expression. The term "regulatory elements" includes a promoter for initiating transcription, any operator sequence for controlling transcription, a sequence encoding suitable mRNA ribosome binding sites, and a sequence for controlling termination of transcription and translation. Examples of this vector include, but are not limited to, plasmid vectors, cosmid vectors, bacteriophage vectors, and viral vectors.

As used herein, the term "recombinant vector" refers to a recombinant vector that may be transformed into a suitable host cell, and then may replicate regardless of the genome of the host cell or may be integrated into the genome itself. In this case, the "suitable host cell" may contain a replication origin, which is a particular nucleotide sequence which enables the vector to replicate in the suitable host cell and from which replication starts.

The transformation may be performed using a suitable vector introduction technique selected depending on the host cell, so that the targeted gene may be expressed in the host cell. For example, introduction of the vector may be performed by electroporation, heat-shock, calcium phosphate ($CaPO_4$) precipitation, calcium chloride ($CaCl_2$) precipitation, microinjection, polyethylene glycol (PEG) method, DEAE-dextran method, cationic liposome method, lithium acetate-DMSO method, or a combination thereof. For the transformed gene, it does not matter whether the gene is inserted into the chromosome of the host cell or located outside of the chromosome, as long as the gene may be expressed in the host cell.

The host cell may include a cell transfected, transformed, or infected with the recombinant vector or polynucleotide of the present disclosure in vivo or in vitro. The host cell containing the recombinant vector of the present disclosure may be a recombinant host cell, a recombinant cell, or a recombinant microorganism.

In addition, the recombinant vector according to the present disclosure may contain a selection marker. The selection marker may be used to select a transformant (host cell) obtained by transformation with the vector. Since only cells expressing the selection marker may survive in the medium treated with the selection marker, the selection marker may select the transformed cells. Representative examples of the selection marker include, but are not limited to, kanamycin, streptomycin, and chloramphenicol.

Genes inserted into the recombinant vector for transformation according to the present disclosure may be substituted into a host cell such as a microorganism of the genus *Corynebacterium* by homologous recombination crossover.

According to one embodiment of the present disclosure, the host cell may be a strain of the genus *Corynebacterium*, for example, a *Corynebacterium glutamicum* strain.

Another aspect of the present disclosure provides a method for producing L-lysine, the method including steps of: a) culturing the *Corynebacterium glutamicum* mutant strain in a medium; and b) recovering L-lysine from the mutant strain or the medium in which the mutant strain has been cultured.

The culturing may be performed using a suitable medium and culture conditions known in the art, and any person skilled in the art may easily adjust and use the medium and the culture conditions. Specifically, the medium may be a liquid medium, but is not limited thereto. Examples of the culturing method include, but are not limited to, batch culture, continuous culture, fed-batch culture, or a combination thereof.

According to one embodiment of the present disclosure, the medium should meet the requirements of a specific strain in a proper manner, and may be appropriately modified by a person skilled in the art. For the culture medium for the strain of the genus *Corynebacterium*, reference may be made to a known document (Manual of Methods for General Bacteriology, American Society for Bacteriology, Washington D.C., USA, 1981), but is not limited thereto.

According to one embodiment of the present disclosure, the medium may contain various carbon sources, nitrogen sources, and trace element components. Examples of the carbon sources that may be used include: saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, but are not limited thereto. Examples of the nitrogen sources that may be used include compounds containing organic nitrogen such as peptone, yeast extract, meat extract, malt extract, corn steep liquor, soybean meal, and urea, or inorganic compounds such as ammonium sulfate, ammonium chloride, ammonium phosphate, ammonium carbonate, and ammonium nitrate. The nitrogen sources may also be used individually or as a mixture, but are not limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be added to the culture medium. The medium or individual components may be added to the culture medium batchwise or in a continuous manner by a suitable method during culturing, but are not limited thereto.

According to one embodiment of the present disclosure, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present disclosure, in the step of recovering L-lysine from the cultured mutant strain or the medium in which the mutant strain has been cultured, the produced L-lysine may be collected or recovered from the medium using a suitable method known in the art depending on the culture method. Examples of the method include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion).

According to one embodiment of the present disclosure, the step of recovering L-lysine may be performed by centrifuging the culture medium at a low speed to remove biomass and separating the obtained supernatant through ion-exchange chromatography.

According to one embodiment of the present disclosure, the step of recovering L-lysine may include a process of purifying L-lysine.

DETAILED DESCRIPTION

Hereinafter, the present disclosure will be described in more detail. However, this description is provided by way of example only to aid the understanding of the present disclosure, and the scope of the present disclosure is not limited by this illustrative description.

Example 1. Construction of *Corynebacterium glutamicum* Mutant Strain

To construct a *Corynebacterium glutamicum* mutant strain, a *Corynebacterium glutamicum* DS1 strain and *E. coli* DH5a (HIT Competent Cells™, Cat No. RH618) were used.

The *Corynebacterium glutamicum* DS1 strain was cultured in a CM-broth medium (pH 6.8) containing, per liter of distilled water, 5 g of glucose, 2.5 g of NaCl, 5.0 g of yeast extract, 1.0 g of urea, 10.0 g of polypeptone and 5.0 g of beef extract at a temperature of 30° C.

The *E. coli* DH5a was cultured in an LB medium containing, per liter of distilled water, 10.0 g of tryptone, 10.0 g of NaCl and 5.0 g of yeast extract at a temperature of 37° C.

The antibiotics ampicillin, kanamycin and chloramphenicol used were purchased from Sigma, and DNA sequencing was performed by Macrogen.

1-1. Construction of Recombinant Vector

Figure 1:
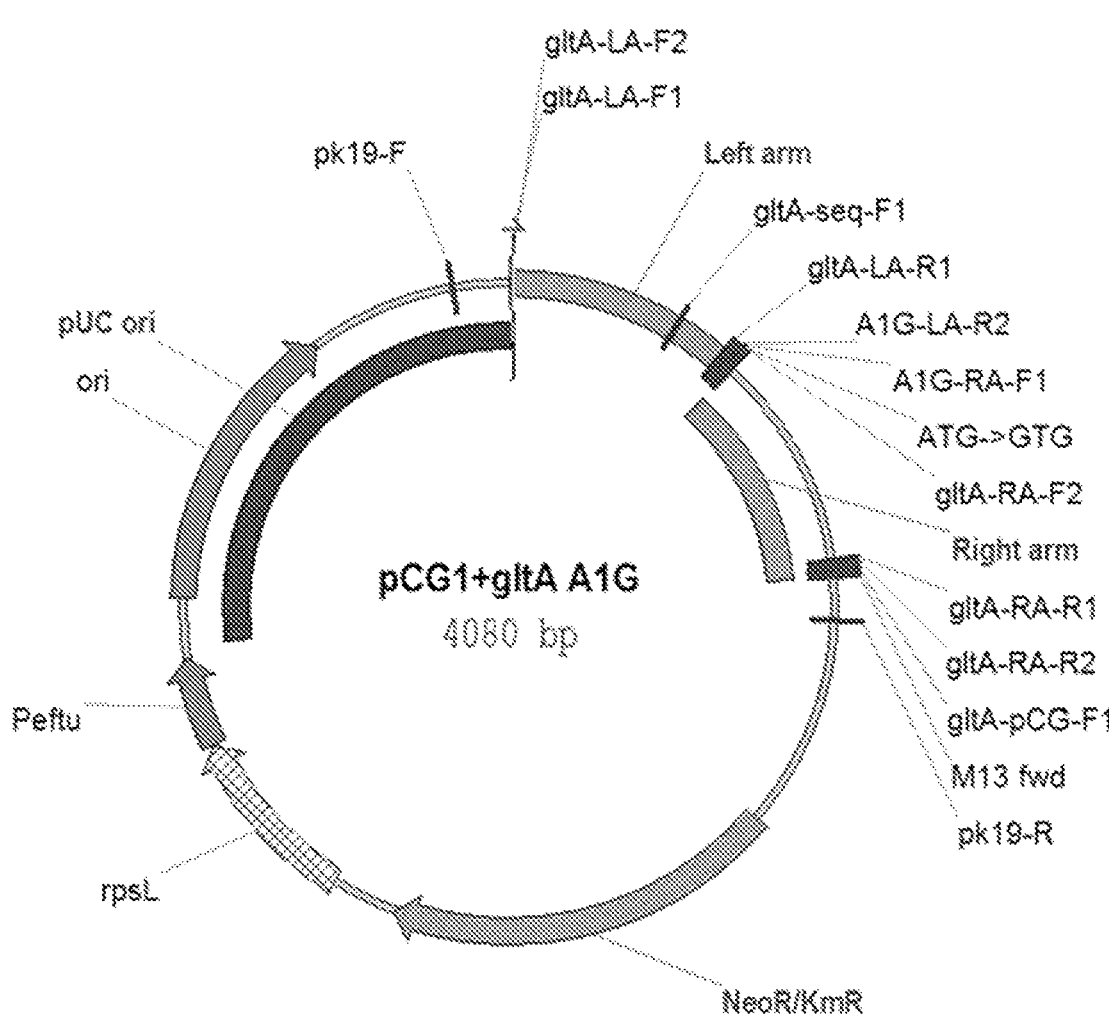
FIG. 1 shows the structure of a pCGI(gltA-A1G) vector containing a citrate synthase (gltA) gene obtained by ATG-to-GTG replacement in the start codon according to one example of the present disclosure.
Figure 2:
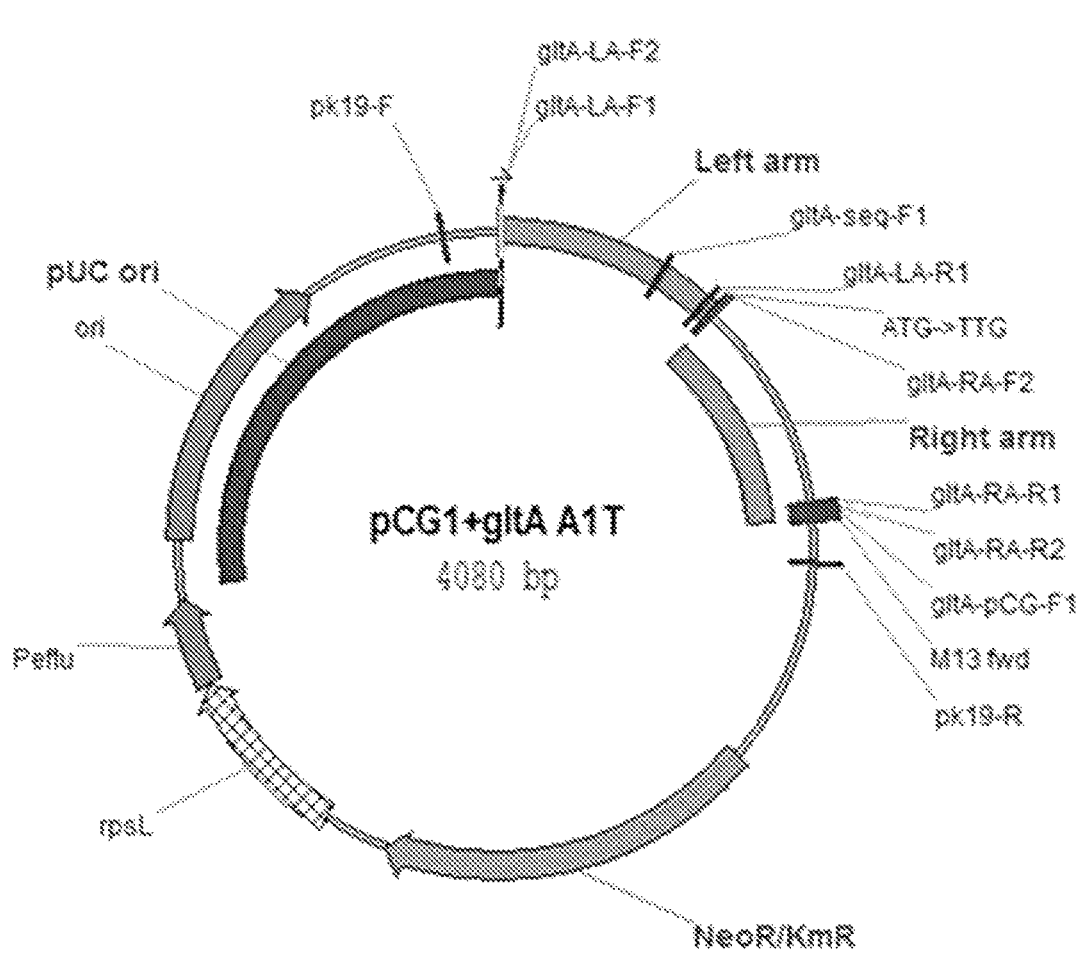
FIG. 2 shows the structure of a pCGI(gltA-A1T) vector containing a citrate synthase (gltA) gene obtained by ATG-to-TTG replacement in the start codon according to one example of the present disclosure.

In order to weaken the TCA cycle in the strain and increase the carbon source efficiency, weakening of the citrate synthase was introduced into the strain. In the method used in this Example, a specific mutation was induced in the translation start codon of the gltA gene encoding the citrate synthase in order to decrease the expression of the gltA gene. The translation start codon of the gltA gene was mutated from ATG to GTG, and a 478-bp region of the left arm and a 475-bp region of the right arm with respect to the center of the gltA gene on the *Corynebacterium glutamicum* genome were amplified by PCR, ligated by overlap PCR, and then cloned into the recombinant vector pCGI (see Kim et al., Journal of Microbiological Methods 84 (2011), 128-130). The resulting plasmid was named pCGI(gltA-A1G) (see FIG. 1). For construction of the plasmid, the primers shown in Table 1 below were used to amplify each gene fragment.

TABLE 1

| | Primer | | SEQ ID NO |
|---|---|---|---|
| Primers for | gltA-LA-F1 | 5'-tgattacgccggttgcgttatagggtggc-3' | 7 |
| amplification | gltA-LA-F2 | 5'-ggttgcgttatagggtggc-3' | 8 |
| of left | gltA-LA-R1 | 5'-ttgttcggaaaaaaactcttcc-3' | 9 |
| homology arm of | A1G-LA-R2 | 5'-tcaaacacatttgttcggaaa-3' | 10 |
| gltA | | | |

TABLE 1-continued

| | Primer | | SEQ ID NO |
|---|---|---|---|
| Primers for | A1G-RA-F1 | 5'-atgtgtttgaaagggatatcgtggctactga-3' | 11 |
| amplification | gltA-RA-F2 | 5'-aagggatatcgtggctactga-3' | 12 |
| of right | gltA-RA-R1 | 5'-agctggtcctggtagtaggtaga-3' | 13 |
| homology arm of | gltA-RA-R2 | 5'-gagtgggttcagctggtcct-3' | 14 |
| gltA | | | |

PCR was performed using the above primers under the following conditions. Using a thermocycler (TP600, TAKARA BIO Inc., Japan), a reaction solution containing 100 µM of each deoxynucleotide triphosphate (dATP, dCTP, dGTP, dTTP), 1 pM of oligonucleotide, and 10 ng of the chromosomal DNA of *Corynebacterium glutamicum* ATCC 13032 as a template, PCR was performed for 25 to 30 cycles in the presence of 1 unit of a pfu-X DNA polymerase mixture (Solgent). The PCR cycles each consisted of (i) denaturation at 94° C. for 30 sec, (ii) annealing at 58° C. for 30 sec, and (iii) extension at 72° C. for 1 to 2 min (a polymerization time of 2 min per kb).

The gene fragments produced as described above were cloned into the pCGI vector by self-assembly cloning. The vector was transformed into *E. coli* DH5a, which was then streaked on an LB-agar plate containing 50 µg/ml of kanamycin, and cultured at 37° C. for 24 hours. The finally formed colonies were isolated and whether the inserts would be exactly present in the vector was examined, and then the vector was isolated and used for recombination of the *Corynebacterium glutamicum* strain.

As the process commonly performed in the above method, the genes of interest was amplified from the genomic DNA of *Corynebacterium glutamicum* ATCC 13032 by PCR and inserted into the pCGI vector by self-assembly cloning according to the strategy, followed by selection in *E. coli* DH5a. For chromosomal base substitution, the gene fragments were amplified individually and ligated by overlap PCR to obtain a target DNA fragment. During genetic manipulation, Ex Taq polymerase (Takara) and Pfu polymerase (Solgent) were used as PCR amplification enzymes, and various restriction enzymes and DNA (see Tauch et al., FEMS Microbiology Letters 123 (1994), 343-347), thus inducing primary recombination. At this time, the electroporated strain was plated on a CM-agar plate containing 20 µg/µl of kanamycin, and the colonies were isolated, and then whether the vector would properly inserted into the induced position on the genome was analyzed by PCR and sequencing. In order to induce secondary recombination, the isolated strain was inoculated into a CM-agar liquid medium containing streptomycin, cultured overnight or longer, and then plated on an agar medium containing streptomycin at the same concentration, and the colonies were isolated. Whether the final isolated colonies would have resistance to kanamycin was examined, and then whether mutation was introduced into the gltA gene in the strains having no antibiotic resistance was analyzed by sequencing (see Schafer et al., Gene 145 (1994), 69-73). Finally, a *Corynebacterium glutamicum* mutant strain (DS2) having the mutant gltA gene introduced therein was obtained.

Example 2. Construction of *Corynebacterium glutamicum* Mutant Strain

A *Corynebacterium glutamicum* mutant strain was constructed in the same manner as in Example 1, except that the start codon of the gltA gene was replaced with TTG.

In this Example, for construction of a plasmid, the primers shown in Table 2 below were used to amplify each gene fragment. A DS2-1 strain, a mutant strain, was constructed using the constructed plasmid pCGI(gltA-A1T) vector. Finally, a *Corynebacterium glutamicum* mutant strain (DS2-1) having the mutant gltA gene introduced therein was obtained.

TABLE 2

| | Primer | | SEQ ID NO |
|---|---|---|---|
| Primers for | gltA-LA-F1 | 5'-tgattacgccggttgcgttatagggtggc-3' | 15 |
| amplification | gltA-LA-F2 | 5'-ggttgcgttatagggtggc-3' | 16 |
| of left | gltA-LA-R1 | 5'-tcaaacaaatttgttcggaaa-3' | 17 |
| homology arm of | A1T-LA-R2 | 5'-atttgtttgaaagggatatcgtggctactga-3' | 18 |
| gltA | | | |
| | | | |
| Primers for | A1T-RA-F1 | 5'-atgtgtttgaaagggatatcgtggctactga-3' | 19 |
| amplification | gltA-RA-F2 | 5'-aagggatatcgtggctactga-3' | 20 |
| of right | gltA-RA-R1 | 5'-agctggtcctggtagtaggtaga-3' | 21 |
| homology arm of | gltA-RA-R2 | 5'-gagtgggttcagctggtcct-3' | 22 |
| gltA | | | | modifying enzymes used were purchased from NEB. These polymerases and enzymes were used according to the supplied buffer and protocols.

1-2. Construction of Mutant Strain

A DS2 strain, a mutant strain, was constructed using the pCGI(gltA-A1G) vector. The vector was prepared at a final concentration of 1 µg/µl or higher, and introduced into the *Corynebacterium glutamicum* DS1 strain by electroporation

Experimental Example 1. Comparison of L-Lysine Productivity Between Mutant Strains L-lysine productivity was compared between the parent strain *Corynebacterium glutamicum* DS1 strain and the lysine-producing mutant strains DS2 and DS2-1 strains constructed in Examples 1 and 2.

The parent strain (DS1) or the mutant strain (DS2 or DS2-1) was inoculated into a 100-ml flask containing 10 ml of a lysine medium having the composition shown in Table 3 below, and then cultured with shaking at 180 rpm at 30° C. for 28 hours. After completion of the culture, the amount of L-lysine produced was measured by HPLC (Shimadzu, Japan), and the results of the measurement are shown in Table 4 below.

TABLE 3

| Composition | Content (per L of distilled water) |
|---|---|
| Glucose | 100 g |
| Ammonium sulfate | 55 g |
| KH$_2$PO$_4$ | 1.1 g |
| MgSO$_4$•H$_2$O | 1.2 9 |
| MnSO$_4$•H$_2$O | 180 mg |
| FeSO$_4$•H$_2$O | 180 mg |
| Thiamine•HCl | 9 mg |
| Biotin | 1.8 mg |
| CaCO$_3$ | 5% |
| pH | 7.0 |

TABLE 4

| Strain | L-lysine (g/L) | L-lysine production per gram dry cell weight (g/gDCW) |
|---|---|---|
| Parent strain (DS1) | 65.2 | 7.0 |
| Mutant strain (DS2) | 69.7 | 7.2 |
| Mutant strain (DS2-1) | 69.8 | 7.2 |

As shown in Table 4 above, it was confirmed that, in the *Corynebacterium glutamicum* mutant strains DS2 and DS2-1 in which the start codon of the gltA gene was replaced with the optimal translation start sequence (GTG or TTG) to improve the lysine biosynthesis pathway, the L-lysine productivities of the mutant strains increased by about 6.9% compared to that of the parent strain *Corynebacterium glutamicum* DS1 strain.

From these results, it could be seen that weakened expression of the gltA gene enhanced L-lysine productivity of the mutant strain by decreasing the metabolic flux of carbon sources.

As described above, the *Corynebacterium glutamicum* mutant strain according to the present disclosure may produce L-lysine in an improved yield by inhibiting the conversion of oxaloacetate to citrate due to decreased or inhibited expression of the gene encoding the citrate synthase.

So far, the present disclosure has been described with reference to the embodiments thereof. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

What is claimed is:

1. A *Corynebacterium glutamicum* mutant strain having enhanced L-lysine productivity due to weakened activity of citrate synthase compared to an unmodified *Corynebacterium glutamicum*, wherein the weakened activity of the citrate synthase is achieved by replacement of a start codon of a gene encoding the citrate synthase comprising the nucleotide sequence of SEQ ID NO: 1 with TTG.

* * * * *

SEQUENCE LISTING

```
<160> NUMBER OF SEQ ID NOS: 22

<210> SEQ ID NO 1
<211> LENGTH: 1314
<212> TYPE: DNA
<213> ORGANISM: Artificial Sequence
<220> FEATURE:
<223> OTHER INFORMATION: Corynebacterium glutamicum gltA

<400> SEQUENCE: 1
atgtttgaaa gggatatcgt ggctactgat aacaacaagg ctgtcctgca ctaccccggt        60
ggcgagttcg aaatggacat catcgaggct tctgagggta acaacggtgt tgtcctgggc       120
aagatgctgt ctgagactgg actgatcact tttgacccag gttatgtgag cactggctcc       180
accgagtcga agatcaccta catcgatggc gatgcgggaa tcctgcgtta ccgcggctat       240
gacatcgctg atctggctga gaatgccacc ttcaacgagg tttcttacct acttatcaac       300
ggtgagctac caaccccaga tgagcttcac aagtttaacg acgagattcg ccaccacacc       360
cttctggacg aggacttcaa gtcccagttc aacgtgttcc cacgcgacgc tcacccaatg       420
gcaaccttgg cttcctcggt taacattttg tctacctact accaggacca gctgaaccca       480
ctcgatgagg cacagcttga taaggcaacc gttcgcctca tggcaaaggt tccaatgctg       540
gctgcgtacg cacaccgcgc acgcaagggt gctccttaca tgtacccaga caactccctc       600
aatgcgcgtg agaacttcct gcgcatgatg ttcggttacc caaccgagcc atacgagatc       660
gacccaatca tggtcaaggc tctggacaag ctgctcatcc tgcacgctga ccacgagcag       720
aactgctcca cctccaccgt tcgtatgatc ggttccgcac aggccaacat gtttgtctcc       780
atcgctggtg gcatcaacgc tctgtccggc ccactgcacg gtggcgcaaa ccaggctgtt       840
ctggagatgc tcgaagacat caagagcaac cacggtggcg acgcaaccga gttcatgaac       900
```

```
aaggtcaaga acaaggaaga cggcgtccgc ctcatgggct tcggacaccg cgtttacaag     960
aactacgatc cacgtgcagc aatcgtcaag gagaccgcac acgagatcct cgagcacctc    1020
ggtggcgacg atcttctgga tctggcaatc aagctggaag aaattgcact ggctgatgat    1080
tacttcatct cccgcaagct ctacccgaac gtagacttct acaccggcct gatctaccgc    1140
gcaatgggct tcccaactga cttcttcacc gtattgttcg caatcggtcg tctgccagga    1200
tggatcgctc actaccgcga gcagctcggt gcagcaggca acaagatcaa ccgcccacgc    1260
caggtctaca ccggcaacga atcccgcaag ttggttcctc gcgaggagcg ctaa          1314
```

```
<210> SEQ ID NO 2
<211> LENGTH: 437
<212> TYPE: PRT
<213> ORGANISM: Artificial Sequence
<220> FEATURE:
<223> OTHER INFORMATION: Corynebacterium glutamicum gltA

<400> SEQUENCE: 2

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
            115                 120                 125

Gln Phe Asn Val Phe Pro Arg Asp Ala His Pro Met Ala Thr Leu Ala
        130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
        210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
            275                 280                 285

Ser Asn His Gly Gly Asp Ala Thr Glu Phe Met Asn Lys Val Lys Asn
```

```
            290                  295                  300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
                340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
                420                 425                 430

Pro Arg Glu Glu Arg
        435
```

```
<210> SEQ ID NO 3
<211> LENGTH: 1314
<212> TYPE: DNA
<213> ORGANISM: Artificial Sequence
<220> FEATURE:
<223> OTHER INFORMATION: Corynebacterium glutamicum gltA - substituted
      ATG with GTG

<400> SEQUENCE: 3
gtgtttgaaa gggatatcgt ggctactgat aacaacaagg ctgtcctgca ctaccccggt     60
ggcgagttcg aaatggacat catcgaggct tctgagggta acaacggtgt tgtcctgggc    120
aagatgctgt ctgagactgg actgatcact tttgacccag ttatgtgag cactggctcc    180 accgagtcga agatcaccta atcgatggc gatgcgggaa tcctgcgtta ccgcggctat    240
gacatcgctg atctggctga gaatgccacc ttcaacgagg tttcttacct acttatcaac    300
ggtgagctac caaccccaga tgagcttcac aagtttaacg acgagattcg ccaccacacc    360
cttctggacg aggacttcaa gtcccagttc aacgtgttcc cacgcgacgc tcacccaatg    420
gcaaccttgg cttcctcggt taacattttg tctacctact accaggacca gctgaaccca    480
ctcgatgagg cacagcttga taaggcaacc gttcgcctca tggcaaaggt tccaatgctg    540
gctgcgtacg cacaccgcgc acgcaagggt gctccttaca tgtacccaga caactccctc    600
aatgcgcgtg agaacttcct gcgcatgatg ttcggttacc caaccgagcc atacgagatc    660
gacccaatca tggtcaaggc tctggacaag ctgctcatcc tgcacgctga ccacgagcag    720
aactgctcca cctccaccgt tcgtatgatc ggttccgcac aggccaacat gtttgtctcc    780
atcgctggtg gcatcaacgc tctgtccggc ccactgcacg gtggcgcaaa ccaggctgtt    840
ctggagatgc tcgaagacat caagagcaac cacggtggcg acgcaaccga gttcatgaac    900
aaggtcaaga acaaggaaga cggcgtccg ctcatgggct cggacaccg cgtttacaag    960 aactacgatc cacgtgcagc aatcgtcaag gagaccgcac acgagatcct cgagcacctc   1020
ggtggcgacg atcttctgga tctggcaatc aagctggaag aaattgcact ggctgatgat   1080
tacttcatct cccgcaagct ctacccgaac gtagacttct acaccggcct gatctaccgc   1140
gcaatgggct tcccaactga cttcttcacc gtattgttcg caatcggtcg tctgccagga   1200
```

-continued

```
tggatcgctc actaccgcga gcagctcggt gcagcaggca acaagatcaa ccgcccacgc      1260
caggtctaca ccggcaacga atcccgcaag ttggttcctc gcgaggagcg ctaa            1314
```

```
<210> SEQ ID NO 4
<211> LENGTH: 437
<212> TYPE: PRT
<213> ORGANISM: Artificial Sequence
<220> FEATURE:
<223> OTHER INFORMATION: Corynebacterium glutamicum gltA - substituted
      ATG with GTG

<400> SEQUENCE: 4

Val Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
            115                 120                 125

Gln Phe Asn Val Phe Pro Arg Asp Ala His Pro Met Ala Thr Leu Ala
        130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
        210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335
```

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
        370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 5
<211> LENGTH: 1314
<212> TYPE: DNA
<213> ORGANISM: Artificial Sequence
<220> FEATURE:
<223> OTHER INFORMATION: Corynebacterium glutamicum gltA - substituted
      ATG with TTG

<400> SEQUENCE: 5
ttgtttgaaa gggatatcgt ggctactgat aacaacaagg ctgtcctgca ctaccccggt      60
ggcgagttcg aaatggacat catcgaggct tctgagggta acaacggtgt tgtcctgggc     120
aagatgctgt ctgagactgg actgatcact tttgacccag ttatgtgag cactggctcc     180 accgagtcga agatcaccta catcgatggc gatgcgggaa tcctgcgtta ccgcggctat     240
gacatcgctg atctggctga gaatgccacc ttcaacgagg tttcttacct acttatcaac     300
ggtgagctac caaccccaga tgagcttcac aagtttaacg acgagattcg ccaccacacc     360
cttctggacg aggacttcaa gtcccagttc aacgtgttcc cacgcgacgc tcacccaatg     420
gcaaccttgg cttcctcggt taacattttg tctacctact accaggacca gctgaaccca     480
ctcgatgagg cacagcttga taaggcaacc gttcgcctca tggcaaaggt tccaatgctg     540
gctgcgtacg cacaccgcgc acgcaagggt gctccttaca tgtacccaga caactccctc     600
aatgcgcgtg agaacttcct cgcgcatgatg ttcggttacc caaccgagcc atacgagatc     660
gacccaatca tggtcaaggc tctggacaag ctgctcatcc tgcacgctga ccacgagcag     720
aactgctcca cctccaccgt tcgtatgatc ggttccgcac aggccaacat gtttgtctcc     780
atcgctggtg gcatcaacgc tctgtccggc ccactgcacg gtggcgcaaa ccaggctgtt     840
ctggagatgc tcgaagacat caagagcaac cacggtggcg acgcaaccga gttcatgaac     900
aaggtcaaga acaaggaaga cggcgtccgc ctcatgggct cggacaccg cgtttacaag     960 aactacgatc cacgtgcagc aatcgtcaag gagaccgcac acgagatcct cgagcacctc    1020
ggtggcgacg atcttctgga tctggcaatc aagctggaag aaattgcact ggctgatgat    1080
tacttcatct cccgcaagct ctacccgaac gtagacttct acaccggcct gatctaccgc    1140
gcaatgggct tcccaactga cttcttcacc gtattgttcg caatcggtcg tctgccagga    1200
tggatcgctc actaccgcga gcagctcggt gcagcaggca acaagatcaa ccgcccacgc    1260
caggtctaca ccggcaacga atcccgcaag ttggttcctc gcgaggagcg ctaa          1314

<210> SEQ ID NO 6
<211> LENGTH: 437

-continued

<212> TYPE: PRT
<213> ORGANISM: Artificial Sequence
<220> FEATURE:
<223> OTHER INFORMATION: Corynebacterium glutamicum gltA - substituted
     ATG with TTG

<400> SEQUENCE: 6

```
Leu Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380
```

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 7
<211> LENGTH: 29
<212> TYPE: DNA
<213> ORGANISM: Artificial Sequence
<220> FEATURE:
<223> OTHER INFORMATION: gltA-LA-F1 primer

<400> SEQUENCE: 7
tgattacgcc ggttgcgtta tagggtggc                                    29

<210> SEQ ID NO 8
<211> LENGTH: 19
<212> TYPE: DNA
<213> ORGANISM: Artificial Sequence
<220> FEATURE:
<223> OTHER INFORMATION: gltA-LA-F2 primer

<400> SEQUENCE: 8
ggttgcgtta tagggtggc                                               19

<210> SEQ ID NO 9
<211> LENGTH: 22
<212> TYPE: DNA
<213> ORGANISM: Artificial Sequence
<220> FEATURE:
<223> OTHER INFORMATION: gltA-LA-R1 primer

<400> SEQUENCE: 9
ttgttcggaa aaaaactctt cc                                           22

<210> SEQ ID NO 10
<211> LENGTH: 21
<212> TYPE: DNA
<213> ORGANISM: Artificial Sequence
<220> FEATURE:
<223> OTHER INFORMATION: A1G-LA-R2 primer

<400> SEQUENCE: 10
tcaaacacat ttgttcggaa a                                            21

<210> SEQ ID NO 11
<211> LENGTH: 31
<212> TYPE: DNA
<213> ORGANISM: Artificial Sequence
<220> FEATURE:
<223> OTHER INFORMATION: A1G-RA-F1 primer

<400> SEQUENCE: 11
atgtgtttga aagggatatc gtggctactg a                                 31

<210> SEQ ID NO 12
<211> LENGTH: 21
<212> TYPE: DNA
<213> ORGANISM: Artificial Sequence
<220> FEATURE:

-continued

<223> OTHER INFORMATION: gltA-RA-F2 primer

<400> SEQUENCE: 12
aagggatatc gtggctactg a                                                          21

<210> SEQ ID NO 13
<211> LENGTH: 23
<212> TYPE: DNA
<213> ORGANISM: Artificial Sequence
<220> FEATURE:
<223> OTHER INFORMATION: gltA-RA-R1 primer

<400> SEQUENCE: 13
agctggtcct ggtagtaggt aga                                                        23

<210> SEQ ID NO 14
<211> LENGTH: 20
<212> TYPE: DNA
<213> ORGANISM: Artificial Sequence
<220> FEATURE:
<223> OTHER INFORMATION: gltA-RA-R2 primer

<400> SEQUENCE: 14
gagtgggttc agctggtcct                                                            20

<210> SEQ ID NO 15
<211> LENGTH: 29
<212> TYPE: DNA
<213> ORGANISM: Artificial Sequence
<220> FEATURE:
<223> OTHER INFORMATION: gltA-LA-F1 primer

<400> SEQUENCE: 15
tgattacgcc ggttgcgtta tagggtggc                                                  29

<210> SEQ ID NO 16
<211> LENGTH: 19
<212> TYPE: DNA
<213> ORGANISM: Artificial Sequence
<220> FEATURE:
<223> OTHER INFORMATION: gltA-LA-F2 primer

<400> SEQUENCE: 16
ggttgcgtta tagggtggc                                                             19

<210> SEQ ID NO 17
<211> LENGTH: 21
<212> TYPE: DNA
<213> ORGANISM: Artificial Sequence
<220> FEATURE:
<223> OTHER INFORMATION: gltA-LA-R1 primer

<400> SEQUENCE: 17
tcaaacaaat ttgttcggaa a                                                          21

<210> SEQ ID NO 18
<211> LENGTH: 31
<212> TYPE: DNA
<213> ORGANISM: Artificial Sequence
<220> FEATURE:
<223> OTHER INFORMATION: A1T-LA-R2 primer

<400> SEQUENCE: 18
atttgtttga aagggatatc gtggctactg a                                               31

-continued

```
<210> SEQ ID NO 19
<211> LENGTH: 31
<212> TYPE: DNA
<213> ORGANISM: Artificial Sequence
<220> FEATURE:
<223> OTHER INFORMATION: A1T-RA-F1 primer

<400> SEQUENCE: 19
atgtgtttga aagggatatc gtggctactg a                                31

<210> SEQ ID NO 20
<211> LENGTH: 21
<212> TYPE: DNA
<213> ORGANISM: Artificial Sequence
<220> FEATURE:
<223> OTHER INFORMATION: gltA-RA-F2 primer

<400> SEQUENCE: 20
aagggatatc gtggctactg a                                           21

<210> SEQ ID NO 21
<211> LENGTH: 23
<212> TYPE: DNA
<213> ORGANISM: Artificial Sequence
<220> FEATURE:
<223> OTHER INFORMATION: gltA-RA-R1 primer

<400> SEQUENCE: 21
agctggtcct ggtagtaggt aga                                         23

<210> SEQ ID NO 22
<211> LENGTH: 20
<212> TYPE: DNA
<213> ORGANISM: Artificial Sequence
<220> FEATURE:
<223> OTHER INFORMATION: gltA-RA-R2 primer

<400> SEQUENCE: 22
gagtgggttc agctggtcct                                             20
```